United States Patent [19]

Nagano et al.

[11] Patent Number: 4,938,795
[45] Date of Patent: * Jul. 3, 1990

[54] TETRAHYDROPHTHALIMIDE COMPOUNDS, AND THEIR PRODUCTION AND USE

[75] Inventors: Eiki Nagano, Nishinomiya; Shunichi Hashimoto, Toyonaka; Ryo Yoshida, Kawanishi; Hiroshi Matsumoto, Toyonaka; Katsuzo Kamoshita, Toyono, all of Japan

[73] Assignee: Sumitomo Chemical Company, Limited, Osaka, Japan

[*] Notice: The portion of the term of this patent subsequent to Jun. 2, 2004 has been disclaimed.

[21] Appl. No.: 942,703

[22] Filed: Dec. 17, 1986

Related U.S. Application Data

[63] Continuation of Ser. No. 473,755, Mar. 9, 1983, Pat. No. 4,670,046, which is a continuation-in-part of Ser. No. 445,726, Nov. 30, 1982, abandoned.

[30] Foreign Application Priority Data

| Dec. 25, 1981 | [JP] | Japan | 56-212396 |
| Jan. 29, 1982 | [JP] | Japan | 57-13845 |
| Feb. 5, 1982 | [JP] | Japan | 57-17858 |
| Mar. 23, 1982 | [JP] | Japan | 57-46940 |
| May 6, 1982 | [JP] | Japan | 57-76306 |

[51] Int. Cl.$^5$ .............. A01N 43/38; C07D 209/48
[52] U.S. Cl. ............................... 71/96; 548/513
[58] Field of Search ......................... 548/513; 71/96

[56] References Cited

U.S. PATENT DOCUMENTS

| 3,235,605 | 2/1966 | Napolitano | 564/440 |
| 3,465,001 | 9/1969 | Bolhofer et al. | 548/513 |
| 3,654,302 | 4/1972 | Schwartz et al. | 548/513 |
| 3,808,230 | 4/1974 | Podesva et al. | 548/476 |
| 3,878,224 | 4/1975 | Matsui et al. | 548/513 |
| 3,954,442 | 5/1976 | Becker et al. | 71/98 |
| 3,984,435 | 10/1976 | Matsui et al. | 548/513 |
| 4,001,272 | 4/1977 | Goddard | 71/96 |
| 4,032,326 | 6/1977 | Goddard | 71/96 |
| 4,124,375 | 11/1978 | Bollinger et al. | 71/96 |
| 4,157,256 | 6/1979 | Hiraga et al. | 71/95 |
| 4,292,070 | 9/1981 | Wakabayashi et al. | 71/96 |
| 4,349,377 | 9/1982 | Durr et al. | 71/98 |
| 4,420,327 | 12/1983 | Jikihara et al. | 71/96 |
| 4,431,822 | 2/1984 | Nagano et al. | 71/96 |
| 4,439,229 | 3/1984 | Swithenbank | 71/96 |
| 4,484,940 | 11/1984 | Nagano et al. | 71/96 |
| 4,484,941 | 11/1927 | Nagano et al. | 71/96 |
| 4,536,209 | 8/1985 | Jikihara et al. | 71/96 |
| 4,563,535 | 1/1986 | Takemoto | 71/96 |
| 4,737,512 | 4/1988 | Hoefle | 548/513 |
| 4,770,695 | 9/1988 | Nagano et al. | 71/96 |

FOREIGN PATENT DOCUMENTS

| 0049508 | 4/1982 | European Pat. Off. . |
| 0049511A | 4/1982 | European Pat. Off. . |
| 061741A | 10/1982 | European Pat. Off. . |
| 067352 | 12/1982 | European Pat. Off. . |
| 068822A | 1/1983 | European Pat. Off. . |
| 077938A | 4/1983 | European Pat. Off. . |
| 83055 | 7/1983 | European Pat. Off. . |
| 126419 | 11/1984 | European Pat. Off. . |
| 2433013 | 3/1980 | France . |
| 57-024355 | 2/1982 | Japan . |
| 59-101405 | 6/1984 | Japan . |
| 213814 | 8/1968 | U.S.S.R. . |
| 2005668 | 4/1979 | United Kingdom . |
| 2046754 | 2/1980 | United Kingdom . |
| 8000341 | 3/1980 | World Int. Prop. O. . |

OTHER PUBLICATIONS

J. Am. Chem. Soc., vol. 81, pp. 94–101 (1959), Finger et al.
C. Swithenbank, Chem. Abstracts vol. 98, No. 215478w (1983).
G. Pagani et al., Il Farmaco-Ed. Sc. vol. 33, pp. 332–349.
G. Pagani et al., Chem. Abst. 89:42719j (1978).
R. Giraudon, Chem. Abst. 93:114150z (1980).
R. Morrison et al., Org. Chemistry, 2nd Ed. p. 602.

*Primary Examiner*—Mary E. Ceperley
*Attorney, Agent, or Firm*—Birch, Stewart, Kolasch & Birch

[57] ABSTRACT

A tetrahydrophthalimide compound of the formula:

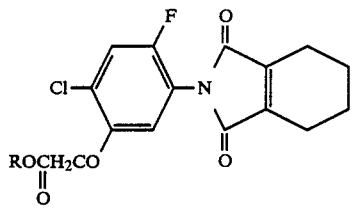

wherein R is methyl or n-pentyl, which is useful as a post emergent herbicide for soybean field.

12 Claims, No Drawings

TETRAHYDROPHTHALIMIDE COMPOUNDS, AND THEIR PRODUCTION AND USE

This application is a continuation of application Ser. No. 473,755, filed on Mar. 9, 1983, now U.S. Pat. No. 4,670,046, which is a continuation-in-part application of our copending application Ser. No. 445,726 filed on Nov. 30, 1982.

The present invention relates to tetrahydrophthalimide compounds, and their production and use.

The said tetrahydrophthalimide compounds (hereinafter referred to as "tetrahydrophthalimide(s)") are representable by the formula:

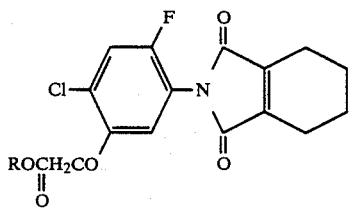
(I)

wherein R is methyl or n-pentyl.

It is known that some tetrahydrophthalimide compounds exhibit a herbicidal activity. For instance, U.S. Pat. No. 3,984,435, EP No. 0049508A, U.S. Pat. Nos. 4,032,326, and 4,439,229, etc. disclose that 2-(4-chlorophenyl)-4,5,6,7-tetrahydro-2H-isoindole-1,3-dione, 2-[4-chloro-3-(1-propylthiocarbonylbutoxy)phenyl]-4,5,6,7-tetrahydro-2H-isoindole-1,3-dione, 2-(4-chloro-2-fluoro)-4,5,6,7-tetrahydro-2H-isoindole-1,3-dione, 2-(4-chloro-5-cyanomethoxy-2-fluorophenyl)-4,5,6,7-tetrahydro-2H-isoindole-1,3-dione, etc. are useful as herbicides. However, their herbicidal effect is not always satisfactory.

It has now been found that the tetrahydrophthalimides (I) show a strong herbicidal activity against a wide variety of weeds by foliar treatment in plowed fields. Advantageously, the tetrahydrophthalimides (I) do not produce any material phytotoxicity on soybean. Their herbicidal activity is particularly notable on post-emergence foliar treatment of broad-leaved weeds such as common purslane (*Portulaca oleracea*), common lambsquarters (*Chenopodium album*), redroot pigweed (*Amaranthus retroflexus*), hemp sesbania (*Sesbania exaltata*), velvetleaf (*Abutilon theophrasti*), prickly sida (*Sida spinosa*), ivyleaf morningglory (*Ipomoea hederacea*), tall morningglory (*Ipomoea purpurea*), field bindweed (*Convolvulus arvensis*), jimsonweed (*Datura stramonium*), black nightshade (*Solanum nigrum*), cocklebur (*Xanthium pensylvanicum*), sunflower (*Helianthus annuus*), and common ragweed (*Ambrosia artemisifolia*) in soybean fields as they do not afford any toxicity to soybean.

The tetrahydrophthalimides (I) can be produced by reacting a hydroxyphenyltetrahydrophthalimide of the formula:

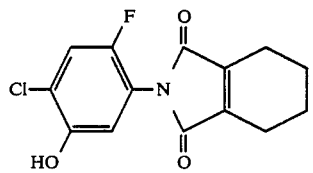
(II)

with an α-haloacetic acid ester of the formula:

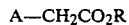

A—CH₂CO₂R  (III)

wherein A is chlorine or bromine and R is as defined above in a solvent in the presence of a dehydrohalogenating agent, usually at a temperature of 0° to 200° C. for 1 to 240 hours. The amounts of the α-haloacetic acid ester (III) and the dehydrohalogenating agent may be respectively 1.0 to 10 equivalents with respect and 0.5 to 1.5 equivalents to the hydroxyphenyltetrahydrophthalimide (II). When desired, a phase transfer catalyst such as tetrabutylammonium bromide or benzyltributylammonium chloride may be employed.

As the solvent, there may be used an aliphatic hydrocarbon (e.g. hexane, heptane, ligroin, petroleum ether), an aromatic hydrocarbon (e.g. benzene, toluene, xylene), a halogenated hydrocarbon (e.g. chloroform, carbon tetrachloride, dichloroethane, chlorobenzene, dichlorobenzene), an ether (e.g. diethyl ether, diisopropyl ether, dioxane, tetrahydrofuran, diethylene glycol dimethyl ether), a ketone (e.g. acetone, methylethylketone, methylisobutylketone, isophorone, cyclohexanone), an alcohol (e.g. methanol, ethanol, isopropanol, t-butanol, octanol, cyclohexanol, methylcellosolve, diethylene glycol, glycerol), a nitrile (e.g. acetonitrile, isobutyronitrile), an acid amide (e.g. formamide, N,N-dimethylformamide, acetamide), a sulfur compound (e.g. dimethylsulfoxide, sulfolane), water, etc. They may be employed alone or in combination.

Examples of the dehydrohalogenating agent are an organic base (e.g pyridine, triethylamine, N,N-diethylaniline), an inorganic base (e.g. sodium hydroxide, potassium hydroxide, sodium carbonate, potassium carbonate, sodium hydride), an alkali metal alkoxide (e.g. sodium methoxide, sodium ethoxide), etc.

The produced tetrahydrophthalimide (I) is, when desired, purified by a per se conventional procedure such as chromatography or recrystallization.

The starting hydroxyphenyltetrahydrophthalimide (II) can be produced from a phenol of the formula:

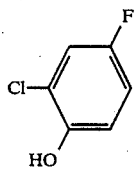
(IV)

according to the following scheme:

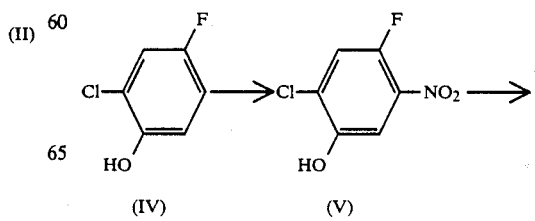

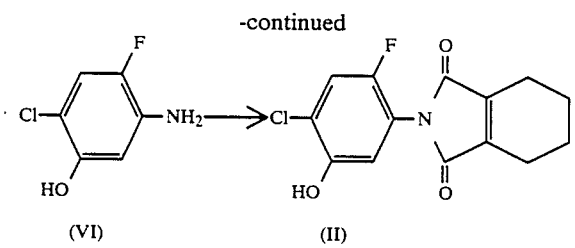

Namely, the hydroxyphenyltetrahydrophthalimide (II) can be manufactured from the phenol (IV) by nitrating the same, reducing the resultant nitrophenol (V) and reacting the resulting aminophenol (VI) with 3,4,5,6-tetrahydrophthalic anhydride.

Conversion of the phenol (IV) into the nitrophenol (V) may be accomplished by application of a per se conventional nitration procedure to the former. Usually, however, the indirect nitration which consists of the following three steps is favorable in achievement of the selective nitration at the desired position:

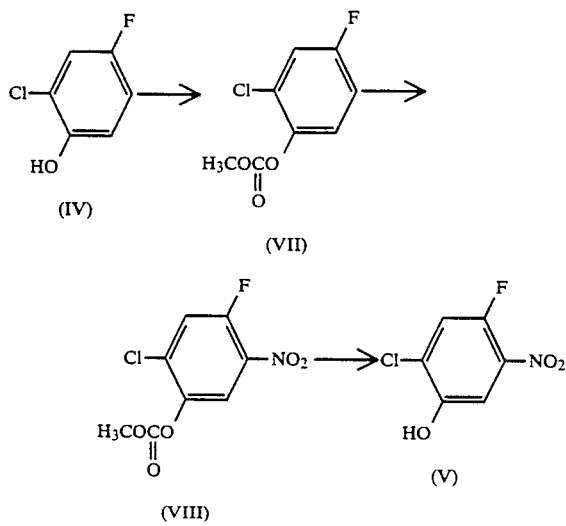

Thus, the phenol (IV) is converted into its alkali metal salt by treatment with an aqueous solution of an alkali metal hydroxide (e.g. sodium hydroxide, potassium hydroxide), and the resulting salt is reacted with an alkyl haloformate such as methyl chloroformate in water at a temperature of 0° to 10° C. The thus prepared carbonic ester (VII) is nitrated with a mixture of conc. sulfuric acid and conc. nitric acid at room temperature. Then, the nitrobenzene (VIII) thus obtained is hydrolyzed with an aqueous alkaline solution such as an aqueous sodium hydroxide solution at a temperature of 20° to 120° C. to give the nitrophenol (V).

Conversion of the nitrophenol (V) into the aminophenol (VI) may be accomplished by any per se conventional reduction procedure for changing a nitro group to an amino group. Examples of such reduction procedure are catalytic reduction, reduction with iron powder, reduction with sodium sulfide, reduction with sulfurated sodium borohydride, etc. For instance, treatment of one molar amount of the nitrophenol (V) with a 3 molar amount of hydrogen in the presence of a 1/10 to 1/100 molar amount of platinum dioxide in an inert solvent (e.g. ethanol, ethyl acetate) at room temperature under atmospheric pressure affords the aminophenol (VI). Further, for instance, treatment of one molar amount of the nitrophenol (V) with a 2 to 5 molar amount of iron powder such as reductive iron or electrolytic iron in a 5% acetic acid solution or a dilute hydrochloric acid solution at a temperature of 80° to 100° C. for a period of 1 to 5 hours produces the aminophenol (VI).

For production of the hydroxyphenyltetrahydrophthalimide (II) from the aminophenol (VI), the latter is reacted with 3,4,5,6-tetrahydrophthalic anhydride in an inert solvent (e.g. acetic acid, water) while refluxing for a period of 1 to 6 hours, preferably of 2 to 4 hours.

In any event, the phenol (IV) is known (cf. Finger et al.: J. Am. Chem. Soc., 81, 94 (1959)).

Practical and presently preferred embodiments for production of the tetrahydrophthalimides (I) as well as the intermediary compounds are illustratively shown in the following Examples.

EXAMPLE 1

2-(4-Chloro-2-fluoro-5-hydroxyphenyl)-4,5,6,7-tetrahydro-2H-isoindole-1,3-dione (3 g) was dissolved in dimethylformamide (100 ml), and anhydrous potassium carbonate (0.8 g) was added thereto. To the resultant mixture was added methyl bromoacetate (1.8 g), and the mixture was heated at 70°-80° C. for 3 hours. After being allowed to cool, water was added to the mixture, which was then extracted with ether, and the extract was washed with water, dried and concentrated. The residue was purified by silica gel column chromatography to give 1.3 g of 2-(4-chloro-2-fluoro-5-methoxycarbonylmethoxyphenyl)-4,5,6,7-tetrahydro-2H-isoindole-1,3-dione (Compound No. 1). M.P., 98°-99.5° C.

In the same manner as above but using n-pentyl bromoacetate in place of methyl bromoacetate, there was produced 2-(4-chloro-2-fluoro-5-n-pentoxycarbonylmethoxyphenyl)-4,5,6,7-tetrahydro-2H-isoindole-1,3-dione (Compound No. 2). M.P., 90°-91° C.

EXAMPLE 2

Production of the hydroxyphenyltetrahydrophthalimide (II)

2-Chloro-4-fluoro-5-aminophenol (6.6 g) and 3,4,5,6-tetrahydrophthalic anhydride (6 g) were dissolved in acetic acid (20 ml) and refluxed for 2 hours. The resultant mixture was allowed to cool to room temperature and poured into ice-water, followed by extraction with ether. The ether extract was washed with a saturated sodium hydrogen carbonate solution and water in order, dried over anhydrous magnesium sulfate and concentrated. The residue was purified by silica gel chromatography to give 4.0 g of N-(4-chloro-2-fluoro-5-hydroxyphenyl)-3,4,5,6-tetrahydrophthalimide. M.P., 151° C.

NMR (CDCl$_3$, D$_6$-DMSO) δ (ppm): 1.5-2.0 (4H, m), 2.1-2.6 (4H, m), 6.8 (1H, d, J=6 Hz), 7.15 (1H, d, J=10 Hz).

IR $\nu_{max}^{nujol}$ (cm$^{-1}$): 3380, 1680.

EXAMPLE 3

Production of the nitrophenol (V)

2-Chloro-4-fluorophenol (83.4 g) was added to a solution of sodium hydroxide (27.7 g) in water (450 ml), and methyl chloroformate (69.2 g) was dropwise added thereto at a temperature below 10° C. Precipitated crystals were collected by filtration and washed with water to give methyl (2-chloro-4-fluorophenyl)formate (134.8 g). M.P., 69°–71° C.

Methyl (2-chloro-4-fluorophenyl)formate (134.8 g) obtained above was suspended in conc. sulfuric acid (50 ml). To the suspension, a mixture of conc. sulfuric acid (50 ml) and conc. nitric acid (50 ml) was added at about 30° C., and the mixture was stirred for 1 hour at this temperature. The reaction mixture was poured into ice-water, and precipitated crystals were collected and washed with water. Methyl (2-chloro-4-fluoro-5-nitrophenyl)formate (143 g) was thus obtained. M.P., 53°–55° C.

The product obtained as above was combined with sodium hydroxide (27 g) and water (300 ml), and the resultant mixture was refluxed for 4 hours. Precipitated insoluble materials were filtered using a celite, and the filtrate was acidified with conc. hydrochloric acid. Precipitated crystals were collected by filtration and washed with water to obtain 76.3 g of 2-chloro-4-fluoro-5-nitrophenol. M.P. 106°–107° C.

NMR (CDCl$_3$, D$_6$-DMSO) $\delta$ (ppm): 7.25 (1H, d, J=10 Hz), 7.64 (1H, d, J=6 Hz).

IR $\nu_{max}^{nujol}$ (cm$^{-1}$): 3370.

EXAMPLE 4

Production of the aminophenol (VI)

A suspension of 2-chloro-4-fluoro-5-nitrophenol (9.17 g) and platinum dioxide (500 mg) in ethanol (120 ml) was subjected to catalytic reduction with hydrogen at room temperature and atmospheric pressure until a designed amount of hydrogen was absorbed. The catalyst was removed by filtration, and the filtrate was concentrated. The residue was extracted with ether, and the ether layer was concentrated to obtain 6.6 g of 3-amino-6-chloro-4-fluorophenol. M.P., 145°–146° C. (decomp.).

NMR (CDCl$_3$, D$_6$-DMSO) $\delta$ (ppm): 6.4 (1H, d, J=8 Hz), 6.85 (1H, d, J=11 Hz).

IR $\nu_{max}^{nujol}$ (cm$^{-1}$): 3400, 3320.

In the practical usage of the tetrahydrophthalimides (I), they may be applied in any composition such as emulsifiable concentrates, wettable powders or suspensions.

The concentration of the active ingredient in such composition is usually within a range of 1 to 95% by weight, preferably of 5 to 80% by weight.

In formulation of those compositions, a solid or liquid carrier or diluent may be used. As the solid carrier or diluent, there may be employed fine dust or granules of kaolin clay, attapulgite clay, bentonite, terra alba, pyrophyllite, talc, diatomaceous earth, calcite, walnut powder, urea, ammonium sulfate, synthetic hydrated silicon dioxide, etc. As the liquid carrier or diluent, there may be employed aromatic hydrocarbons (e.g. xylene, methylnaphthalene), alcohols (e.g. isopropanol, ethylene glycol, cellosolve), ketones (e.g. acetone, cyclohexanone, isophorone), plant oils (e.g. soybean oil, cottonseed oil), dimethylsulfoxide, acetonitrile, water, etc.

A surface active agent used for emulsification, dispersion or spreading may be any of the non-ionic, anionic, cationic and amphoteric type of agents. Examples of the surface active agent include alkylsulfates, alkylaryl sulfonates, dialkylsuccinates, polyoxyethylene alkylaryl phosphates, polyoxyethylene alkyl ethers, polyoxyethylene alkylaryl ethers, polyoxyethylene-polyoxypropylene blocked polymers, sorbitan fatty acid esters, polyoxyethylene sorbitan fatty acid esters, polyoxyethylene resin acid esters, abietic acid, dinaphthylmethanedisulfonates, paraffin and the like. If necessary, ligninsulfonates, alginates, polyvinyl alcohol, gum arabic, CMC (carboxymethylcellulose), PAP (isopropyl acid phosphate) or the like may be used as an auxiliary agent.

Practical embodiments of the herbicidal composition according to the invention are illustratively shown in the following examples wherein part(s) and % are by weight.

FORMULATION EXAMPLE 1

Eighty parts of Compound No. 1, 5 parts of polyoxyethylene alkylaryl ether and 15 parts of synthetic hydrated silicon dioxide are well mixed while being powdered to obtain a wettable powder.

FORMULATION EXAMPLE 2

Ten parts of Compound No. 2, 7 parts of polyoxyethylene alkylaryl ether, 3 parts of alkylarylsulfonate and 80 parts of cyclohexanone are well mixed to obtain an emulsifiable concentrate.

FORMULATION EXAMPLE 3

Twenty parts of Compound No. 2 is mixed with 60 parts of an aqueous solution containing 3% of polyoxyethylene sorbitan monooleate and pulverized until the particle size of the active ingredient becomes less than 3 microns. Twenty parts of an aqueous solution containing 3% of sodium alginate as a dispersing agent are incorporated therein to obtain a suspension.

FORMULATION EXAMPLE 4

Fifty parts of Compound No. 1, 3 parts of calcium ligninsulfonate, 2 parts of sodium laurylsulfate and 45 parts of synthetic hydrated silicon dioxide are well mixed while being powdered to obtain a wettable powder.

FORMULATION EXAMPLE 5

Ten parts of Compound No. 2, 14 parts of polyoxyethylene styrylphenyl ether, 6 parts of calcium dodecylbenzenesulfonate, 30 parts of xylene and 40 parts of cyclohexanone are well mixed to obtain an emulsifiable concentrate.

These compositions comprising the tetrahydrophthalimides (I) may be applied, after dilution with water, to the weeds in suitable application modes such as spraying. For instance, they may be applied for foliar treatment. If necessary, they may be used together with other herbicides to improve their activity as herbicides, and in some cases, a synergistic effect can be expected. They may be also applied in combination with insecticides, acaricides, nematocides, fungicides, plant growth regulators, fertilizers, soil controlling agents, etc.

A dosage rate of the tetrahydrophthalimide (I) as the active ingredient may be generally from 0.01 to 100 grams, preferably from 0.05 to 10 grams, per are. In the practical usage of the tetrahydrophthalimide (I) as emulsifiable concentrates, wettable powders or suspensions, it may be diluted with 1 to 10 liters of water (optionally including an auxiliary agent such as a spreading agent) per are.

The application of the tetrahydrophthalimides (I) as herbicides will be illustratively shown in the following Examples wherein the phytotoxicity to cultivated plants and the herbicidal activity on weeds were evaluated as follows: the aerial parts of the test plants were cut off and weighed (fresh weight); the percentage of the fresh weight of the treated plant to that of the untreated plant was calculated with the latter fresh weight taken as 100; and the phytotoxicity and the herbicidal activity were evaluated by the standard given in the table below.

| Rating value | Fresh weight (percentage to untreated plot) (%) | |
|---|---|---|
| | Herbicidal activity | Phytotoxicity |
| 0 | 91– | 91– |
| 1 | 71–90 | 71–90 |
| 2 | 41–70 | 51–70 |
| 3 | 11–40 | 31–50 |
| 4 | 1–10 | 11–30 |
| 5 | 0 | 0–10 |

The following compounds were used in the Examples for comparison:

| Compound No. | Structure | Remarks |
|---|---|---|
| (a) | [2-fluoro-4-chlorophenyl tetrahydrophthalimide] | U.S. Pat. No. 4,032,326 |
| (b) | [4-chlorophenyl tetrahydrophthalimide] | U.S. Pat. No. 3,984,435 |
| (c) | [chlorophenyl tetrahydrophthalimide with (n)H7C3—S—C(=O)—CH(OC3H7(n)) substituent] | EP 0049508A |
| (d) | [2,4,5-trichlorophenyl-OCH2COONa] | Commercially available herbicide known as "2,4,5-T" (Na salt) |
| (e) | [benzothiadiazinone with N—CH(CH3)2, SO2, N—Na] | Commercially available herbicide known as "Bentazone" (Na salt) |
| (f) | [F3C, Cl-phenyl-O-phenyl with COONa and NO2] | Commercially available herbicide known as "Acifluorfen-sodium" |
| (g) | [2-fluoro-4-chloro-5-(NCH2CO)phenyl tetrahydrophthalimide] | U.S. Pat. No. 4,439,229 |

TEST EXAMPLE 1

Trays (33×23 cm²) were filled with upland field soil, and the seeds of soybean, tall morningglory, velvet-leaf, black nightshade, cocklebur and hemp sesbania were sowed therein and grown for 18 days in a greenhouse. A designed amount of the test compound formulated into an emulsifiable concentrate according to Formulation Example 2 and diluted with water was sprayed to the foliage of the test plants over the top by means of a small hand sprayer at a spary volume of 10 liters per are. At the time of application, the test plants were generally at the 2 to 4 leaf stage and had a height of 2 to 12 cm. Twenty days thereafter, herbicidal activity and phytotoxicity were examined. The results are shown in Table 1.

TABLE 1

| Compound No. | Dosage (weight of active ingredient, g/are) | Phytotoxicity Soybean | Herbicidal activity | | | | |
|---|---|---|---|---|---|---|---|
| | | | Tall morning-glory | Velvet-leaf | Black night-shade | Cocklebur | Hemp sesbania |
| 1 | 0.4 | 1 | 5 | 5 | 5 | 5 | 5 |
| | 0.2 | 0 | 5 | 5 | 5 | 5 | 5 |
| 2 | 0.4 | 0 | 5 | 5 | 5 | 5 | 5 |
| | 0.2 | 0 | 5 | 5 | 5 | 4 | 5 |
| (a) | 0.4 | 3 | 4 | 5 | 4 | 3 | 2 |
| | 0.2 | 1 | 2 | 4 | 3 | 1 | 1 |
| (b) | 0.4 | 0 | 1 | 4 | 1 | 0 | 2 |
| (c) | 0.4 | 1 | 1 | 5 | 2 | 0 | 2 |
| (d) | 0.4 | 2 | 2 | 2 | 1 | 0 | 3 |
| (f) | 2.5 | 2 | 5 | 2 | 4 | 4 | 5 |
| | 0.63 | 0 | 3 | 0 | 1 | 1 | 5 |

TEST EXAMPLE 2

Trays (33×23 cm²) were filled with upland field soil, and the seeds of soybean, tall morningglory, velvet-leaf, black nightshade, sunflower and hemp sesbania were sowed therein and grown for 20 days in a greenhouse. A designed amount of the test compound formulated into an emulsifiable concentrate accordng to Formulation Example 5 and diluted with water was sprayed to the foliage of the test plants over the top by means of a small hand sprayer at a spray volume of 10 liters per are. At the time of application, the test plants were generally at the 2 to 3 leaf stage and had a height of 5 to 15 cm. Fifteen days thereafter, herbicidal activity and phytotoxicity were examined. The results are shown in Table 2.

TABLE 2

| Compound No. | Dosage (weight of active ingredient, g/are) | Phytotoxicity Soybean | Herbicidal activity | | | | |
|---|---|---|---|---|---|---|---|
| | | | Tall morning-glory | Velvet-leaf | Black night-shade | Sunflower | Hemp sesbania |
| 1 | 0.08 | 0 | 4 | 4 | 2 | 2 | 2 |
| | 0.32 | 1 | 5 | 5 | 4 | 4 | 4 |
| | 1.25 | 2 | 5 | 5 | 5 | 5 | 5 |
| 2 | 0.08 | 0 | 4 | 5 | 3 | 2 | 2 |
| | 0.32 | 1 | 5 | 5 | 4 | 4 | 4 |
| | 1.25 | 2 | 5 | 5 | 5 | 5 | 5 |
| (g) | 0.08 | 3 | 4 | 4 | 4 | 3 | 3 |
| | 0.32 | 4 | 5 | 5 | 5 | 4 | 3 |
| | 1.25 | 4 | 5 | 5 | 5 | 5 | 5 |

TEST EXAMPLE 3

The seeds of soybean, cocklebur, tall morningglory, velvetleaf, jimson weed, redroot pigweed, sunflower, common ragweed and common lambsquarters were sowed in the field as previously laid up in ridges, each ridge plotted in 3 m². When soybean, cocklebur and other plants were grown at the 1-2 compound leaf stage, 6-leaf stage and 4-9 leaf stage, respectively, a designed amount of the test compound formulated into an emulsifiable concentrate according to Formulation Example 5 and diluted with water (including a spreading agent) was sprayed to the foliage of the test plants by means of a small hand sprayer at a spray volume of 5 liters per are with three replications. Thirty days thereafter, herbicidal activity and phytotoxicity were examined. The results are shown in Table 3.

TABLE 3

| Compound No. | Dosage (weight of active ingredient, g/are) | Phytotoxicity Soybean | Herbicidal activity | | | | | | | |
|---|---|---|---|---|---|---|---|---|---|---|
| | | | Cocklebur | Tall morning-glory | Velvet-leaf | Jimson weed | Redroot pigweed | Sunflower | Common ragweed | Common lambsquarters |
| 1 | 1 | 1 | 5 | 5 | 5 | 5 | 5 | 5 | 5 | 5 |
| | 0.5 | 1 | 4 | 5 | 5 | 5 | 5 | 5 | 5 | 5 |
| 2 | 1 | 1 | 5 | 5 | 5 | 5 | 5 | 5 | 5 | 5 |
| | 0.5 | 0 | 5 | 5 | 5 | 5 | 5 | 5 | 5 | 5 |
| (e) | 10 | 1 | 5 | 3 | 5 | 5 | 2 | 5 | 5 | 5 |

TABLE 3-continued

| Compound No. | Dosage (weight of active ingredient, g/are) | Phyto-toxicity Soybean | Herbicidal activity | | | | | | | |
|---|---|---|---|---|---|---|---|---|---|---|
| | | | Cocklebur | Tall morning-glory | Velvet-leaf | Jimson weed | Redroot pigweed | Sun-flower | Common rag-weed | Common lambs-quarters |
| | 5 | 0 | 5 | 1 | 5 | 5 | 0 | 5 | 5 | 3 |

What is claimed is:

1. A herbicidal composition which comprises as an active ingredient a herbicidally effective amount of a compound of the formula:

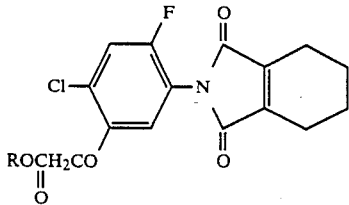

wherein R is methyl or n-pentyl and an inert carrier.

2. A compound of the formula:

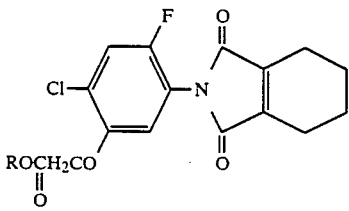

wherein R is methyl or n-pentyl.

3. A compound according to claim 2, which is 2-(4-Chloro-2-fluoro-5-methoxycarbonylmethoxy-phenyl)-4,5,6,7-tetrahydro-2H-isoindole-1,3-dione.

4. A compound according to claim 2, which is 2-(4-Chloro-2-fluoro-5-n-pentyloxycarbonyl-methoxy-phenyl)-4,5,6,7-tetrahydro-2H-isoindole-1,3-dione.

5. The herbicidal composition according to claim 1, wherein R is methyl.

6. The herbicidal composition according to claim 1, wherein R is n-pentyl.

7. A method for controlling or exterminating weeds by post-emergence application in a soybean field which comprises applying to said field a compound of the formula:

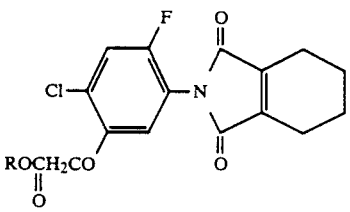

wherein R is methyl or n-pentyl at a dosage rate of 0.2 to 1.25 grams per 100 m².

8. A method according to claim 7, wherein said dosage rate is 0.2 to 0.4 grams per 100 m².

9. A method according to claim 7, wherein R is methyl.

10. A method according to claim 8, wherein R is methyl.

11. A method according to claim 7, wherein R is n-pentyl.

12. A method according to claim 8, wherein R is n-pentyl.

* * * * *